United States Patent
Bharadwaj et al.

(10) Patent No.: US 10,688,494 B2
(45) Date of Patent: Jun. 23, 2020

(54) MICROFLUIDIC SURFACE-MEDIATED EMULSION STABILITY CONTROL

(71) Applicant: 10X Genomics, Inc., Pleasanton, CA (US)

(72) Inventors: Rajiv Bharadwaj, Pleasanton, CA (US); Tobias Daniel Wheeler, Alameda, CA (US); Kevin Ness, Pleasanton, CA (US); Benjamin Hindson, Pleasanton, CA (US)

(73) Assignee: 10X Genomics, Inc., Pleasanton, CA (US)

( * ) Notice: Subject to any disclaimer, the term of this patent is extended or adjusted under 35 U.S.C. 154(b) by 0 days.

(21) Appl. No.: 16/325,922

(22) PCT Filed: Aug. 23, 2017

(86) PCT No.: PCT/US2017/048202
§ 371 (c)(1),
(2) Date: Feb. 15, 2019

(87) PCT Pub. No.: WO2018/039338
PCT Pub. Date: Mar. 1, 2018

(65) Prior Publication Data
US 2019/0176152 A1  Jun. 13, 2019

Related U.S. Application Data

(60) Provisional application No. 62/378,490, filed on Aug. 23, 2016.

(51) Int. Cl.
| | | |
|---|---|---|
| *C12Q 1/68* | (2018.01) | |
| *B01L 3/00* | (2006.01) | |
| *B01F 13/00* | (2006.01) | |
| *B01J 2/06* | (2006.01) | |
| *C12Q 1/6844* | (2018.01) | |
| *B01F 3/08* | (2006.01) | |

(52) U.S. Cl.
CPC ...... *B01L 3/502784* (2013.01); *B01F 3/0807* (2013.01); *B01F 3/0811* (2013.01); *B01F 13/0086* (2013.01); *B01J 2/06* (2013.01); *C12Q 1/6844* (2013.01); *B01F 2215/0037* (2013.01); *B01L 2200/0673* (2013.01); *B01L 2200/12* (2013.01); *B01L 2200/16* (2013.01); *B01L 2300/16* (2013.01)

(58) Field of Classification Search
CPC ............ C12Q 1/6844; C12Q 2531/113; C12Q 2563/179; C12Q 2565/629; B01F 13/0086; B01F 2215/0037; B01F 3/0807; B01F 3/0811; B01J 2/06; B01L 2200/0673; B01L 2200/12; B01L 2200/16; B01L 2300/16; B01L 3/502784
See application file for complete search history.

(56) References Cited

U.S. PATENT DOCUMENTS

| | | |
|---|---|---|
| 2014/0206554 A1 | 7/2014 | Hindson et al. |
| 2014/0227684 A1 | 8/2014 | Hindson et al. |
| 2014/0228255 A1 | 8/2014 | Hindson et al. |
| 2015/0005199 A1 | 1/2015 | Hindson et al. |
| 2015/0292988 A1* | 10/2015 | Bharadwaj ............ B01L 3/0241 506/27 |
| 2016/0199832 A1* | 7/2016 | Jamshidi .................. B41J 2/04 204/450 |

FOREIGN PATENT DOCUMENTS

| | | |
|---|---|---|
| EP | 2962751 A | 1/2016 |
| WO | 2014/028537 A1 | 2/2014 |
| WO | 2015/200717 A2 | 12/2015 |

OTHER PUBLICATIONS

International Search Report and Written Opinion dated Oct. 27, 2017 for International Patent Application No. PCT/US2017/048202.
Quere, David. "Wetting and Roughness," Annu. Rev. Mater. Res. 2008. 38:71-99.
Zhao, Meng-Hua et al. "Wetting failure of hydrophilic surfaces promoted by surface roughness," Sci. Rep. 4, 5376 (2014).
Chu, Kuang-Han et al. "Uni-directional liquid spreading on asymmetric nanostructured surfaces," Nature Materials, vol. 9 (2010), 413-417.

* cited by examiner

*Primary Examiner* — Cynthia B Wilder
(74) *Attorney, Agent, or Firm* — Clark & Elbing LLP

(57) ABSTRACT

A microfluidic emulsion droplet generation system and methods of use thereof are provided. The system may include a microfluidic substrate having a flow path configured and arranged for emulsion droplet generation, at least one textured surface in the flow path configured and arranged for inducing surface-mediated coalescence of emulsion droplets; and at least one channel junction in the flow path for emulsion droplet formation.

43 Claims, 3 Drawing Sheets

MICROFLUIDIC SURFACE-MEDIATED EMULSION STABILITY CONTROL

CROSS-REFERENCE TO RELATED APPLICATIONS

This application is a U.S. national stage of International Patent Application No. PCT/US2017/048202, filed Aug. 23, 2017, which claims priority to and the benefit of U.S. Provisional Patent Application No. 62/378,490, filed Aug. 23, 2016, each of which is incorporated herein by reference in its entirety.

BACKGROUND

The field of microfluidics has advanced to the point that it is fulfilling much of its promise to supplant conventional laboratory fluid handling. The ability to precisely control the movement, accession, allocation, and mixing of minute amounts of fluids and subject those fluids to additional processing, analysis, and the like has helped move the field into the mainstream of scientific research, diagnostics, and medical devices.

As research and diagnostic needs become more and more complex, however, there is a need for the field of microfluidics to similarly advance in complexity, requiring a wide range of new functionalities within the microfluidic context. By way of example, microfluidic systems have been used to deliver and combine reagents within microfluidic channels and then perform subsequent processing and/or analytical operations on those reagents, including, e.g., thermal cycling, separations, optical, chemical or electrical detection, and a host of other operations.

In other applications, microfluidic systems have been used to partition small aliquots of aqueous fluids within flowing streams of immiscible fluids, e.g., oils, in order to compartmentalize reactions within those partitions for separate processing, analysis, etc. Specific implementations of these systems have been used to compartmentalize individual nucleic acids in order to perform quantitative amplification and detection reactions (qPCR).

In another implementation, the GEMCODE™ system from 10× GENOMICS®, discrete droplets in an emulsion contain both template nucleic acids and beads bearing large numbers of oligonucleotide barcodes, where a given bead will have a constant barcode sequence. The barcode is then used to prime replication of fragments of the template molecules within the particular partition. The replicate fragments created within a given droplet will all share the same barcode sequence, allowing replicate fragments from single long template molecules to be attributed to that longer template. Sequencing of the replicate fragments then provides barcode linked-reads that can be later attributed back to an originating long fragment, provide long range sequence context for shorter sequence reads.

Surface wettability of substrates is an important physical property for the design of microfluidic droplet-based assays. Surface wettability can influence droplet generation as well as droplet/emulsion stability. Typically, the surface wettability and emulsion stability is tuned by using surfactants in the dispersed and continuous phases. Surface wettability can also be controlled by coatings and chip materials used. Additionally, the surface roughness/texture also influences emulsion stability especially when the droplets interact with surfaces such as in collection wells of the chips. In particular, roughness induced wetting of surfaces can cause large scale coalescence of emulsion and thereby failed assays.

With increasing demands on microfluidic systems, there is a need to add to the microfluidic tools that can be applied to expand their utility. The present disclosure provides a number of such tools and the uses and applications thereof.

SUMMARY

In general, in one embodiment a microfluidic emulsion droplet generation system is provided including: a microfluidic substrate having a flow path configured and arranged for emulsion droplet generation; at least one textured surface in the flow path configured and arranged for inducing surface-mediated coalescence of emulsion droplets; and at least one channel junction in the flow path for emulsion droplet formation.

In one aspect the at least one textured surface is disposed in the flow path downstream of the channel junction.

In another aspect the substrate further comprises one or more microchannels or reservoirs in the flow path upon which the at least one textured surface is disposed. In a particular aspect the reservoir is an outlet well.

In a further aspect the at least one textured surface in the flow path of the system is a microtexture or a nanotexture surface. In a particular aspect the at least one textured surface is produced in the substrate by injection molding, photolithography, embossing or any combinations thereof. In yet another aspect the at least one textured surface is textured by nano-pillars, nano-cones, nanofibers, nanotubes, microgrooves, striations, tool marks, coatings or any combinations thereof. In a further aspect the at least one textured surface is configured in an array. In another aspect the at least one textured surface provides for spontaneous wetting, superhydrophobicity, superoleophobicity, interfacial slip or any combinations thereof.

In one embodiment one or more cross-sectional dimensions of the flow path are less than 200 microns. In another aspect one or more cross-sectional dimensions of the flow path are less than 100 microns. In yet another aspect one or more cross-sectional dimensions of the flow path are less than 50 microns.

In general, in another embodiment, a method of emulsion droplet formation using the droplet generation system and aspects thereof as described above is provided including: providing a dispersed phase and a continuous phase to the system; and forming emulsion droplets comprising the dispersed phase and continuous phase in the system.

In one aspect of the method droplet formation is performed without a surfactant in the dispersed phase or continuous phase. In a specific aspect the dispersed phase is aqueous and the continuous phase comprises oil.

In another aspect of the method the at least one textured surface is disposed in the flow path downstream of the channel junction.

In a further aspect of the method the substrate further includes one or more microchannels or reservoirs in the flow path upon which the at least one textured surface is disposed. In a particular aspect the reservoir is an outlet well.

In another aspect of the method the at least one textured surface is a microtexture or a nanotexture. In one aspect the at least one textured surface is produced in the substrate by injection molding, photolithography, embossing or any combinations thereof. In another aspect the at least one textured surface is textured by nano-pillars, nano-cones, nanofibers, nanotubes, microgrooves, striations, tool marks, coatings or any combinations thereof. In a further aspect the at least one textured surface is configured in an array. In yet a further aspect the at least one textured surface provides for spontaneous wetting, superhydrophobicity, superoleophobicity, interfacial slip or any combinations thereof.

In a further aspect of the method one or more cross-sectional dimensions of the flow path are less than 200 microns. In one aspect one or more cross-sectional dimensions of the flow path are less than 100 microns. In another aspect one or more cross-sectional dimensions of the flow path are less than 50 microns.

In another aspect of the method the emulsion droplets include polynucleotides, barcodes, beads or combinations thereof. In one embodiment the polynucleotides and barcodes are attached to the beads. In another embodiment the bead includes a covalent bond that is cleavable upon application of a stimulus. In a particular embodiment the covalent bond is a disulfide bond.

In general, in another aspect a method of emulsion droplet surface-mediated coalescence using the system described above includes: providing a dispersed phase and a continuous phase to the system for emulsion droplet formation; forming emulsion droplets in the system; directing the emulsion droplets to the textured surface; and coalescing the emulsion droplets.

In one aspect the surface-mediated coalescence is achieved without a chemical agent coalescence stimulus. In another aspect the emulsion droplets are coalesced after a reaction performed in the emulsion droplets.

In one embodiment of the method the reaction is a polymerase chain reaction (PCR).

In another embodiment of the method the at least one textured surface is disposed in the flow path downstream of the channel junction.

In yet another embodiment of the method the substrate further includes one or more microchannels or reservoirs in the flow path upon which the at least one textured surface is disposed. In one aspect the reservoir is an outlet well.

In another embodiment of the method the at least one textured surface is a microtexture or a nanotexture. In one aspect the at least one textured surface is produced in the substrate by injection molding, photolithography, embossing or any combinations thereof. In another aspect the at least one textured surface is textured by nano-pillars, nano-cones, nanofibers, nanotubes, microgrooves, striations, tool marks, coatings or any combinations thereof. In a further aspect the at least one textured surface is configured in an array. In another aspect the at least one textured surface provides for spontaneous wetting, superhydrophobicity, superoleophobicity, interfacial slip or any combinations thereof.

In another embodiment of the method one or more cross-sectional dimensions of the flow path are less than 200 microns. In a particular aspect one or more cross-sectional dimensions of the flow path are less than 100 microns. In a further aspect one or more cross-sectional dimensions of the flow path are less than 50 microns.

In another embodiment of the method the emulsion droplets comprise polynucleotides, barcodes, beads or combinations thereof. In one aspect the polynucleotides and barcodes are attached to the beads. In another aspect the bead comprises a covalent bond that is cleavable upon application of a stimulus. In a further aspect the covalent bond is a disulfide bond.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference.

DETAILED DESCRIPTION

I. General Overview

Emulsion Droplets and Reagent Partitioning

Figure 1A:
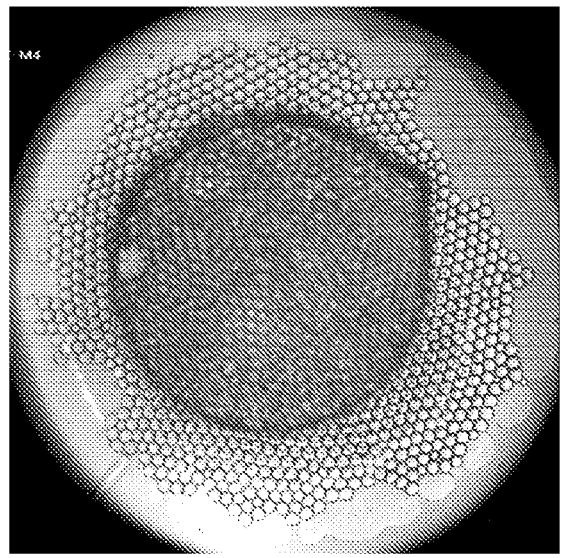
FIGS. 1A and 1B are photomicrographs of microfluidic outlet wells including rough and smooth surface textures respectively and containing emulsion droplets according to example embodiments of the present invention.

The present disclosure provides devices, systems, and methods that are, in some embodiments, particularly useful in managing complex samples for analysis using high throughput analytical systems, including, for example, high throughput nucleic acid analysis systems, such as nucleic acid arrays, nucleic acid sequencing systems, nucleic acid amplification and quantitation systems, or the like. In particular, certain embodiments of the devices, systems, and methods described herein are particularly useful in providing encapsulated reagents or reagent systems, and co-partitioning these reagents with sample components for further reaction and/or analysis. This co-partitioning of reagents and sample components can be used, for example, in reducing the complexity of the sample material by segregating portions of the sample to different partitions. Further, by also segregating reagents, one can subject each sample portion to a different reaction, including for example, the application of unique identifiers to different sample components, e.g., attachment of a discrete barcode or tagging reagents to the discrete sample components.

Particularly elegant examples of these co-partitioning approaches are described in Published International Patent Application No. WO2014/028537, and U.S. Patent Application Publication Nos. US 20140206554, US 20140227684, US 20140228255, and US 20150292988 the full disclosures of each of which are incorporated herein by reference in their entirety for all purposes.

By way of example, one particularly elegant approach provides a polymer microcapsule composition that includes nucleic acid barcode sequences bound to the microcapsule, where the barcodes associated with a given microcapsule have substantially the same sequence of nucleotides, but where different discrete microcapsules will have different barcode sequences associated with such microcapsules. Each of these microcapsules is then contacted with a portion of a sample fluid, such as a sample fluid that includes a template nucleic acid from a sample material. The mixture of sample material including the template nucleic acid and the microcapsule is then partitioned into a small volume, such as a droplet in a water in oil emulsion, such that the microcapsule and a portion of the sample material are contained within the same droplet. In addition to controlling the droplet generation process to provide a desired number of microcapsules in a given partition, the sample material and emulsion process also may be controlled to provide for a desired amount of sample material, e.g., sample nucleic acid material, within each partition, e.g., to provide a single template molecule or a desired level of genome coverage within a given partition, or other desired level of sample materials.

Within the partition, the barcode sequence is reacted with the sample material, e.g., the template nucleic acid to effectively tag the sample material or a portion thereof. For example, by reacting the barcode sequence with the template, e.g., through amplification of the template sequence using the barcode sequence as an extension primer, one can effectively "attach" the barcode sequence to the replicated or amplified template. Similarly, replication of the extended primer produces a complement of the template along with a complement to the barcode, again, effectively attaching the barcode to the template. The presence or attachment of the barcode sequence, or its complement, on or to the amplified template molecule, or its complement, then allows some level of attribution of sequence reads that include that barcode to the same portion of sample material, e.g., the same template molecule or the same sample components, that was originally allocated to that partition.

In many cases, the molecule that includes the barcode sequence or sequences may also include functional elements that are used in subsequent processing of the amplified template sequences. These functional sequences include, for example, primer sequences (e.g., targeted or universal), primer recognition sequences, sequences that can form secondary structures, either within the sequence, or upon replication of the sequence, enrichment sequences, e.g., that are used as affinity purification sequences, immobilization sequences, probe sequences, reverse complement or hairpin sequences, or any of a variety of other functional sequences.

There are a wide variety of other high-value applications for such partitioning and barcoding or tagging processes. The present disclosure advantageously provides devices, systems and methods that can greatly facilitate the generation of such partitioned compositions or components thereof.

II. Fluidic Systems for Producing Encapsulated Reagents and Partitioned Reactions The present disclosure provides improved fluidic systems, and particularly improved microfluidic systems, that are useful for both the generation of encapsulated reagents, as well as in the partitioning of those encapsulated reagents for use in subsequent reactions and/or analyses. As used herein, microfluidic systems typically denote fluidic systems that employ one or more fluid conduits, channels, chambers, or the like that include one or more interior cross-sectional dimensions, e.g., depth, length or width, that are less than 1000 microns, less than 200 microns, less than 100 microns, and in some cases, less than about 50 microns, or even less than about 20 microns. In some cases, one or more cross-sectional dimensions may be about 20 microns or less or 10 microns or less. Typically, these microfluidic channels or chambers will have at least one cross-sectional dimension of between about 1 and about 100 microns.

As will be appreciated, reference to encapsulated reagents is not intended to limit the scope of such reagents to completely enclosed capsules, but is intended to reflect any of a variety of methods of associating reagents with a given particle, bead, or other solid or semi-solid particle phase. In particular, encapsulation generally refers to the entrainment or other attachment, coupling, or association of a particular species with a solid or semi-solid particle, bead, enclosure, partition or droplet, and is not limited to compositions in which the species is entirely or partially enclosed within a larger structure.

In some aspects, encapsulated reagents are associated with microcapsules that are generally spherical in shape, although they may be elongated, plug shaped, or otherwise vary in their specific shape. In some cases, microcapsules will have one or more cross-sectional dimensions that are less than 200 microns, less than 150 microns, or less than about 100 microns. In some cases, microcapsules of the present disclosure have one or more cross-sectional dimensions that are between about 10 and about 200 microns, between about 20 and 150 microns, between about 30 and 125 microns, in many cases between about 40 and about 100 microns, and still other cases, between about 50 and about 75 microns.

While the dimensions of the microcapsules can be an important consideration, in many applications the variability in those dimensions is also an important consideration. In particular, for example, the transport of a microcapsule through a microfluidic system can be significantly impacted by the size of that microcapsule. For example, simple flow resistance may be greater for much larger microcapsules than for smaller microcapsules. Similarly, propensity for clogging may be greater for larger microcapsules than for smaller microcapsules. In either event, flow rates of microcapsules through a microfluidic system may be greatly impacted by the size of the microcapsule. Accordingly, in certain aspects, the microcapsules of described herein, will be provided as a population of microcapsules having substantially monodisperse cross-sectional dimensions. In terms of cross-sectional dimensions, the phrase substantially monodisperse refers to a population that deviates (e.g., expressed as a coefficient of variation and stated as a percentage) from the mean cross-sectional dimension by no more than 50%, no more than 40%, no more than 30%, no more than 20%, or in some cases, no more than 10%.

Whether in the context of generating microcapsules for use in entrainment or encapsulation of reagents, or in the partitioning of aqueous fluids within non-aqueous droplets, the devices and systems of the present disclosure can employ a similar architecture in some embodiments. In a simplified example, this architecture in some embodiments may include a first channel segment that is fluidly connected to a first junction that fluidly connects the first channel segment with a second channel segment and a third channel segment. The second channel segment delivers to the junction a second fluid that is immiscible with the first aqueous fluid, such as an oil, that allows for the formation of aqueous droplets within the stream of immiscible fluid. This second fluid may be referred to herein as the dispersion fluid, partitioning fluid or the like. The flow of the first and second fluids through the junction and into the third channel segment is controlled such that droplets of the first fluid are dispensed into a flowing stream of the second fluid within the third channel segment.

A variety of modifications to this basic structure according to embodiments of the present invention are available to better control droplet formation and to bring in additional fluid streams. As used herein, the control of fluid flows encompasses both active control of fluid flows through the application of greater or lesser driving forces to cause that fluid flow. Additionally, flows may be controlled in whole or in part, by controlling the flow characteristics of one or more of the fluids and/or the conduits through which they are flowing. For example, in some embodiments, fluid flow may be controlled by providing higher flow resistance within a conduit, e.g., through providing a higher viscosity, narrower conduit dimension, or providing larger or smaller microcapsules within a fluid stream, or any combination of the foregoing. In some cases, control is imparted through several of controlled driving force, controlled conduit dimensions, and controlled fluid properties, e.g., viscosity or particle composition.

In microfluidic droplet generation, surfactants are frequently used to prevent the coalescence of droplets to maintain partitioning of reagents. However, in some cases, it is desirable to cause coalescence to occur, such as when bulk biochemical reactions or cleanups of the chemical species of droplets are to be performed after in-droplet reactions. There are various means to cause coalescence, including but not limited to—electric fields, and destabilizing surfactants. However, each of these methods require the addition of chemicals or additional complexity in the form of active elements (such as electrodes for electro-coalescence) in the system. It is sometimes desirable to cause coalescence by passive means. Macro-fluidic example: liquid-liquid separations (Agarwal, S. et al. Separation and Purification Technology 107:19-25 (2013)).

Types of Roughness—Amplitude/Frequency

In general, increasing the roughness of a surface causes a hydrophilic surface to become more hydrophilic and a hydrophobic surface to become more hydrophobic (Quere, D. Annu. Rev. Mater. Res. 38:71-99 (2008); see also Zhao, M. et al. Sci. Rep. 4, 5376; DOI: 10.1038/srep05376 (2014)). The roughness of a surface can be described by the amplitude and the frequency or density of the features causing an increase in the surface area. The frequency of the roughness can be particularly influential on the wettability of a surface, with a higher frequency causing a surface to be more wettable than a lower frequency. According to embodiments of the present invention, this increased wettability can be used to purposefully cause coalescence of microfluidically-generated droplets on the surface. In some embodiments, the roughness may have a frequency of up to one surface feature (e.g., peak) per nanometer distance along the surface. In some embodiments, the roughness may have a frequency of less than one surface feature per nanometer distance along the surface (e.g., one surface feature per 10 nm, 100 nm, 1 μm, etc.). The frequency of the roughness, according to some embodiments, may range from 0.001 to 1 features per nm along the surface. The surface features may have an amplitude (e.g., height) in the nano- or micrometer scale. In some embodiments, the amplitude of the surface features is less than 100 μm. In some embodiments, the amplitude of the surface features is less than 50 μm. In some embodiments, the amplitude of the surface features is less than 10 μm. In some embodiments, the amplitude of the surface features is less than 1 μm. In some embodiments, the amplitude of the surface features at least 10 nm. In some embodiments, the amplitude of the surface features may range from about 10 nm to about 10 μm, from about 10 nm to about 1 μm, from about 10 nm to about 500 nm, or from about 10 nm to about 100 nm. In some embodiments, the amplitude of the surface features may range from about 50 nm to about 5000 nm, from about 50 nm to about 1000 nm, from about 50 nm to about 500 nm, from about 50 nm to about 300 nm, from about 50 nm to about 200 nm, from about 50 nm to about 100 nm. For example, in FIGS. 1A and 1B, the amplitude of the roughness of both exit wells are on the order of 100 nm. However, the frequency of roughness in FIG. 1A, in which coalescence on the well surface occurs, is higher than that of FIG. 1B.

Methods of introducing textured surfaces in a microfluidic substrate according to some embodiments can include, but are not limited to injection molding, photolithography, embossing, sanding, machining, and surface coatings or any combinations thereof. In some embodiments, the surface is textured to have a regular pattern of surface features (e.g., an evenly spaced array of surface features). In other embodiments, the surface may be randomly patterned with surface features such that the distance between individual surface features may vary. In some embodiments, the surface features on a roughened surface may be differently sized/shaped or, in other embodiments, may be similarly sized/shaped. Methods of removing surface roughness include polishing, etching, and surface coatings or any combinations thereof.

Surface texturing can be in the form of, for example, providing defined nano-pillar/cones/nanofibers/nanotubes arrays, microgrooves, striations, tool marks or coatings. In some embodiments, it is also possible and advantageous to provide directional wetting implemented by surface texturing. In some embodiments, direction wetting may be achieved by providing anisotropic nano-scale (e.g., 10 nm to 1000 nm) features on a surface. In some embodiments, the anisotropic features are arranged assymetically on the surface to provide directional wetting. In some embodiments, the surface may be patterned with the features described by Kuang-Han Chu et al., "Uni-directional liquid spreading on asymmetric nanostructured surfaces," Nature Materials 9, 413-417 (2010), which is incorporated by reference herein in its entirety. In some embodiments, directional wetting can be used as a passive valving mechanism which allows wetting of substrates in a desired direction and not in others. This can allow robust priming and reagent loading to the chip by ensuring a well defined initial condition of reagent locations in the channels.

III. Examples

Figure 3A:
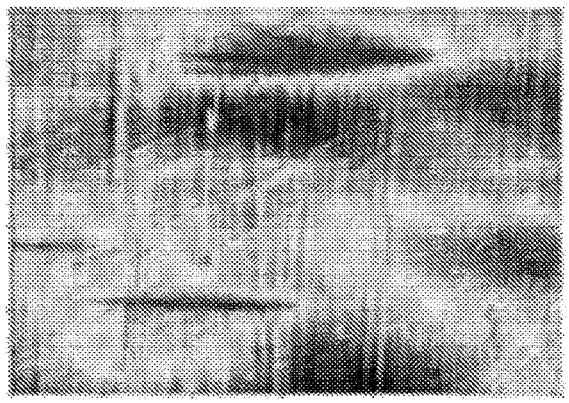
FIGS. 3A-3C are topography images showing example surfaces having smooth surfaces according to embodiments of the present invention.
Figure 4A:
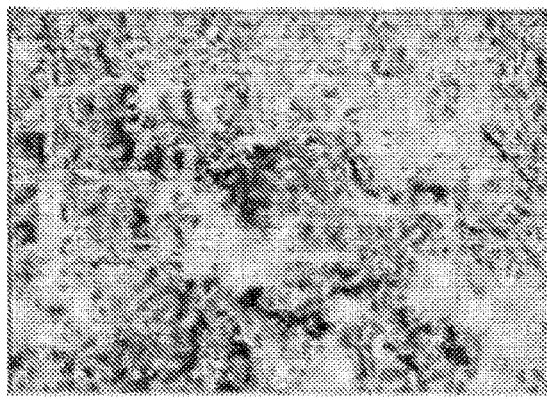
FIGS. 4A-4C are topography images showing example surfaces having roughened surfaces according to embodiments of the present invention.
Figure 3B:
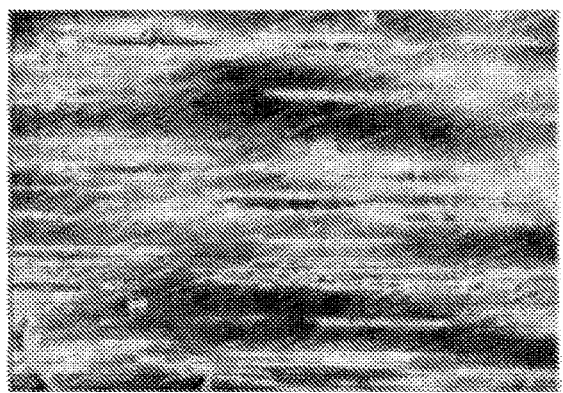
Figure 4B:
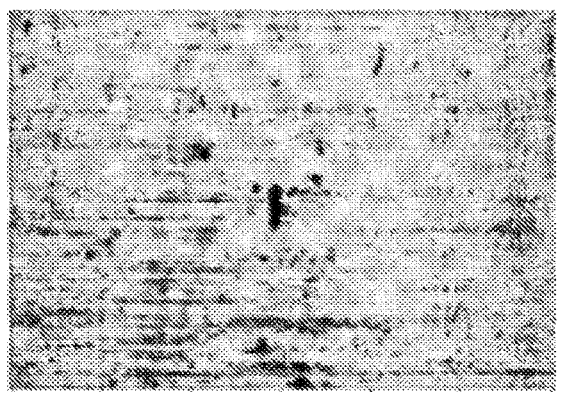
Figure 3C:
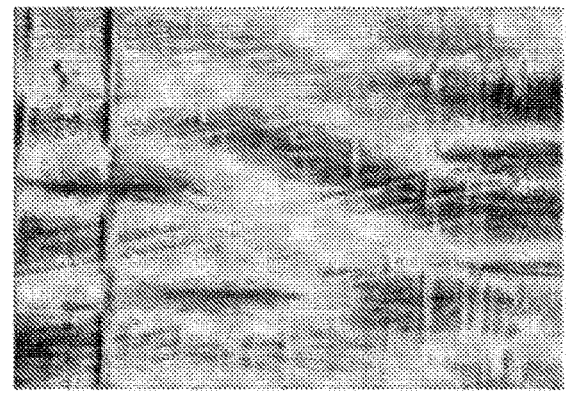
Figure 4C:
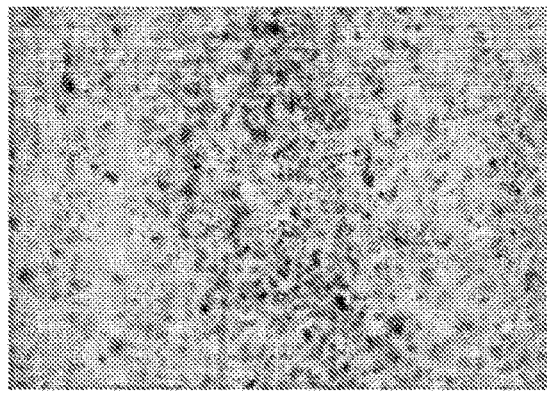

Example 1: Surface-Mediated Coalescence of Emulsion Droplets in Microfluidic Features Surface-mediated coalescence of emulsion droplets containing gel beads (GEMs) was tested in a microfluidic chip substrate including outlet wells for GEMs collection. The GEMs were made up of a gel bead in an aqueous phase surrounded by oil. The aqueous phase included a buffer, enzymes, glycerol, cell lysis surfactant; the oil phase included oil and emulsion-stabilizing surfactant. The microfluidic chips were molded from a thermoplastic material. In a first case, outlet wells were manufactured with a rougher surface texture than in a second case where the outlet wells had a smoother surface texture. Surface roughness of the well was determined by the roughness of the mold used to shape the thermoplastic from which the chips were made, which is in turn was determined by the machining process used to make the mold. Polishing the mold (resulting in smoother surfaces) prevented coalescence. According to white-light interferometry (WLI) measurements, there was no regular pattern to the roughness, the Rt=maximum peak–minimum valley was 0.7 μm-3 μm. Example topography images of the surfaces are shown in FIGS. 3A-4C. FIGS. 3A-3C show topography images of relatively smoother example surfaces which were non-coalescing. FIGS. 4A-4C show topography images of example surfaces with rougher surface texture which resulted in coalescence.

The same number of GEMs were introduced into each type of outlet well. The effect of surface texture on GEMs stability was observed by photomicroscopic viewing of the bottoms of the outlet wells. The effect on stability was visualized by observing the amount of intact vs. coalesced GEMs through the bottom of the outlet wells.

Figure 1B:
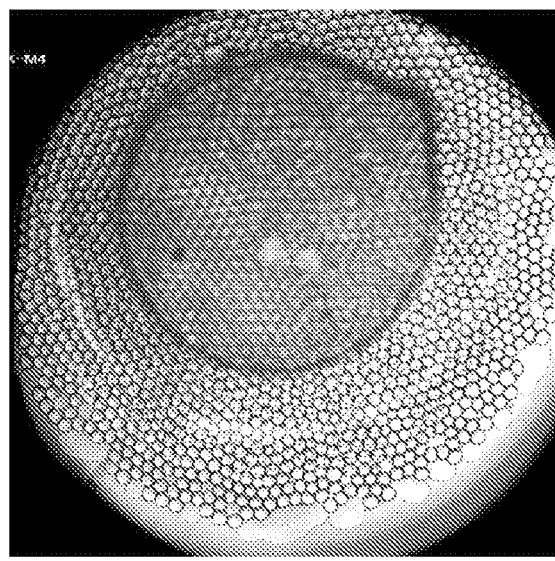

FIGS. 1A and 1B are photomicrographs of the experimental results. FIG. 1A shows an outlet well having a rougher surface texture and GEMs collected therein. FIG. 1B shows a different outlet well having a smoother surface texture and GEMs collected therein. By comparing the two images, it is readily apparent that the GEMs in FIG. 1A are fewer in number as a result of surface-mediated coalescence of the GEMs. Pooled aqueous phase evidencing coalescence of the GEMs in FIG. 1A is much more apparent at the outer edges of the outlet wells than in FIG. 1B.

The results of this study indicated that rougher surface texture correlates with increased coalescence of GEMs, while smoother surface texture supports stability of GEMs. It can be concluded from these results that emulsion droplets, for example GEMs, can be effectively manipulated by microfluidic feature surface roughness/smoothness design. Both stabilization of the emulsion droplets as well as surface-mediated coalescence can be achieved as desired based on application of different surface textures to the microfluidic feature surfaces and interaction with emulsion droplets.

Example 2: Controlled Emulsion Droplet Surface-Mediated Coalescence

In a microfluidic emulsion droplet generation system or device, surface texturing of microfluidic channels, wells or other physical features can provide improved control over emulsion droplet formation. Depending on the desired application, microchannels, wells or other features in a substrate can be configured for superhydrophobicity (providing anti-wetting characteristics) or superhydrophilicity (providing wetting characteristics), which could benefit droplet generation, preservation and coalescence. This could be achieved, for example, by use of nano/micro-structured surface texture within the entire or a portion of the microchannels.

One potential application of this approach is to generate and preserve stable emulsion droplets even in the presence of detergents which would otherwise wet the native microchannel substrate and favor coalescence. Application of surface texture design including smooth to varying degrees of roughness could be used to control emulsion droplet stability even in the presence of detergents or other agents.

Figure 2A:
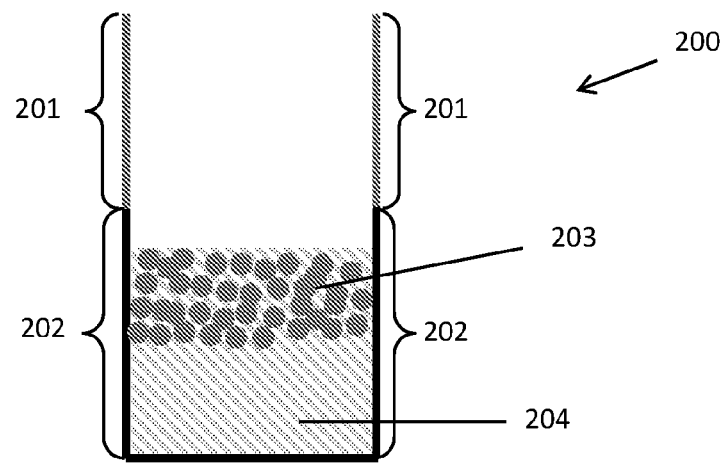
FIGS. 2A and 2B are illustrations of a microfluidic feature including rough and smooth surface textures in series, and showing their effect on emulsion droplets according to an embodiment of the present invention.
Figure 2B:
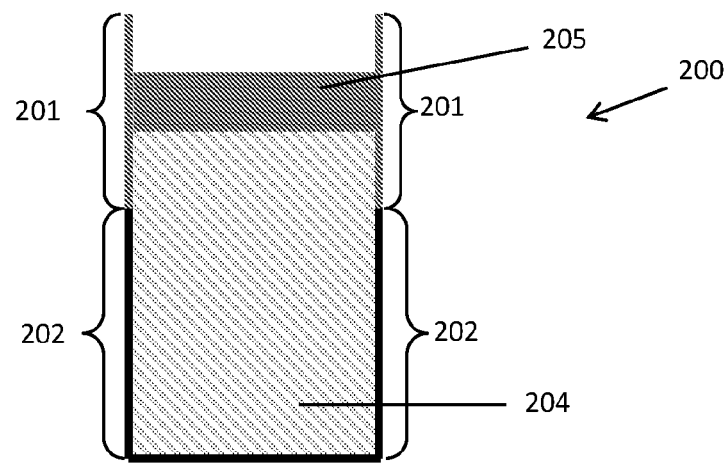

An exemplary design for controlling emulsion droplet surface-mediated coalescence in a microfluidic substrate according to embodiments of the present invention is illustrated in FIGS. 2A and 2B. Microfluidic feature 200 can be, for example, a fluid path, channel, well etc. of a microfluidic system. The microfluidic feature 200 in the example illustrated includes two distinct regions 201, 202 of surface texture. It can be understood that any of a number of configurations would be possible, including two or more distinct regions of surface texture, and spacing of textured surfaces as required for controlling stability of emulsions droplets or for coalescence. Region 202 is relatively smooth in texture. Region 201 is relatively rough in texture in comparison to region 202. The microfluidic feature 200 further includes oil 204 that can be flowed in the feature 200 to transport emulsion droplets 203 in the feature 200.

As shown in FIG. 2A at a first time point the amount of oil 204 provided keeps the emulsion droplets 203 positioned in the smooth surface texture region 202. In this state, the emulsion droplets 203 are stable and can be controlled in such a state while remaining in proximity of the region 202. In FIG. 2B, additional oil 204 has been introduced and the emulsion droplets 203 were driven into the rough surface texture region 201 of the microfluidic feature 200. As illustrated in FIG. 2B, surface-mediated coalescence results in loss of the intact emulsion droplets 203 and formation of coalesced emulsion droplets 205.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A microfluidic emulsion droplet generation system comprising:
    a) a microfluidic substrate having a flow path configured and arranged for emulsion droplet generation;
    b) at least one channel junction in the flow path for emulsion droplet formation; and
    c) a reservoir in the flow path downstream of the channel junction comprising at least one textured surface configured and arranged for inducing surface-mediated coalescence of a plurality of emulsion droplets.

2. The system of claim 1, wherein the reservoir is an outlet well.

3. The system of claim 1, wherein the at least one textured surface is a microtexture or a nanotexture.

4. The system of claim 1, wherein the at least one textured surface is produced in the substrate by injection molding, photolithography, embossing or any combinations thereof.

5. The system of claim 1, wherein the at least one textured surface is textured by nanopillars, nano-cones, nanofibers, nanotubes, microgrooves, striations, tool marks, coatings or any combinations thereof.

6. The system of claim 1, wherein the at least one textured surface is configured in an array.

7. The system of claim 1, wherein the at least one textured surface provides for spontaneous wetting, superhydrophobicity, superoleophobicity, interfacial slip or any combinations thereof.

8. The system of claim 1, wherein one or more cross-sectional dimensions of the flow path are less than 200 microns.

9. The system of claim 1, wherein one or more cross-sectional dimensions of the flow path are less than 100 microns.

10. The system of claim 1, wherein one or more cross-sectional dimensions of the flow path are less than 50 microns.

11. A method of emulsion droplet formation using the droplet generation system of claim 1 comprising:
   a) providing a dispersed phase and a continuous phase to the system; and
   b) forming emulsion droplets comprising the dispersed phase and continuous phase in the system.

12. The method of claim 11, wherein droplet formation is performed without a surfactant in the dispersed phase or continuous phase.

13. The method of claim 11, wherein the dispersed phase is aqueous and the continuous phase comprises oil.

14. The method of claim 11, wherein the reservoir is an outlet well.

15. The method of claim 11, wherein the at least one textured surface is a microtexture or a nanotexture.

16. The method of claim 11, wherein the at least one textured surface is produced in the substrate by injection molding, photolithography, embossing or any combinations thereof.

17. The method of claim 11, wherein the at least one textured surface is textured by nanopillars, nano-cones, nanofibers, nanotubes, microgrooves, striations, tool marks, coatings or any combinations thereof.

18. The method of claim 11, wherein the at least one textured surface is configured in an array.

19. The method of claim 11, wherein the at least one textured surface provides for spontaneous wetting, superhydrophobicity, superoleophobicity, interfacial slip or any combinations thereof.

20. The method of claim 11, wherein one or more cross-sectional dimensions of the flow path are less than 200 microns.

21. The method of claim 11, wherein one or more cross-sectional dimensions of the flow path are less than 100 microns.

22. The method of claim 11, wherein one or more cross-sectional dimensions of the flow path are less than 50 microns.

23. The method of claim 11, wherein the emulsion droplets comprise polynucleotides, barcodes, beads or combinations thereof.

24. The method of claim 23, wherein the polynucleotides and barcodes are attached to the beads.

25. The method of claim 23, wherein the bead comprises a covalent bond that is cleavable upon application of a stimulus.

26. The method of claim 25, wherein the covalent bond is a disulfide bond.

27. A method of emulsion droplet surface-mediated coalescence using the system of claim 1 comprising:
   a) providing a dispersed phase and a continuous phase to the system for emulsion droplet formation;
   b) forming emulsion droplets in the system;
   c) directing the emulsion droplets to the textured surface; and
   d) coalescing the emulsion droplets.

28. The method of claim 27, wherein surface-mediated coalescence is achieved without a chemical agent coalescence stimulus.

29. The method of claim 27, wherein the emulsion droplets are coalesced after a reaction is performed in the emulsion droplets.

30. The method of claim 27, wherein the reaction is a polymerase chain reaction (PCR).

31. The method of claim 27, wherein the reservoir is an outlet well.

32. The method of claim 27, wherein the at least one textured surface is a microtexture or a nanotexture.

33. The method of claim 27, wherein the at least one textured surface is produced in the substrate by injection molding, photolithography, embossing or any combinations thereof.

34. The method of claim 27, wherein the at least one textured surface is textured by nanopillars, nano-cones, nanofibers, nanotubes, microgrooves, striations, tool marks, coatings or any combinations thereof.

35. The method of claim 27, wherein the at least one textured surface is configured in an array.

36. The method of claim 27, wherein the at least one textured surface provides for spontaneous wetting, superhydrophobicity, superoleophobicity, interfacial slip or any combinations thereof.

37. The method of claim 27, wherein one or more cross-sectional dimensions of the flow path are less than 200 microns.

38. The method of claim 27, wherein one or more cross-sectional dimensions of the flow path are less than 100 microns.

39. The method of claim 27, wherein one or more cross-sectional dimensions of the flow path are less than 50 microns.

40. The method of claim 27, wherein the emulsion droplets comprise polynucleotides, barcodes, beads or combinations thereof.

41. The method of claim 40, wherein the polynucleotides and barcodes are attached to the beads.

42. The method of claim 40, wherein the bead comprises a covalent bond that is cleavable upon application of a stimulus.

43. The method of claim 42, wherein the covalent bond is a disulfide bond.

* * * * *